United States Patent
Vittitow et al.

(10) Patent No.: US 11,058,691 B2
(45) Date of Patent: Jul. 13, 2021

(54) NITRIC OXIDE RELEASING PROSTAGLANDIN DERIVATIVES FOR TREATING NORMAL TENSION GLAUCOMA

(71) Applicants: BAUSCH & LOMB INCORPORATED, Rochester, NY (US); NICOX S.A., Valbonne (FR)

(72) Inventors: Jason Lamar Vittitow, Flanders, NJ (US); Megan Elizabeth Cavet, Pittsford, NY (US)

(73) Assignees: Nicox S.A., Valbonne (FR); Bausch & Lomb Incorporated, Rochester, NY (US)

( * ) Notice: Subject to any disclaimer, the term of this patent is extended or adjusted under 35 U.S.C. 154(b) by 134 days.

(21) Appl. No.: 16/343,323

(22) PCT Filed: Nov. 7, 2017

(86) PCT No.: PCT/EP2017/078486
§ 371 (c)(1),
(2) Date: Apr. 18, 2019

(87) PCT Pub. No.: WO2018/087092
PCT Pub. Date: May 17, 2018

(65) Prior Publication Data
US 2020/0179401 A1   Jun. 11, 2020

Related U.S. Application Data

(60) Provisional application No. 62/419,153, filed on Nov. 8, 2016.

(51) Int. Cl.
*A61K 31/5575* (2006.01)
*A61P 27/06* (2006.01)
*A61K 45/06* (2006.01)

(52) U.S. Cl.
CPC .......... *A61K 31/5575* (2013.01); *A61P 27/06* (2018.01); *A61K 45/06* (2013.01)

(58) Field of Classification Search
CPC ............................ A61K 31/5575; A61P 27/06
See application file for complete search history.

(56) References Cited

U.S. PATENT DOCUMENTS

| 7,273,946 | B2* | 9/2007 | Ongini | .............. | C07C 405/0016 560/8 |
| 7,449,469 | B2* | 11/2008 | Ongini | .............. | C07C 405/0016 514/255.01 |
| 7,629,345 | B2* | 12/2009 | Ongini | .................... | A61P 27/06 514/255.01 |
| 7,910,767 | B2* | 3/2011 | Ongini | .............. | C07C 405/0016 560/8 |
| 8,058,467 | B2* | 11/2011 | Ongini | .............. | C07C 405/0016 560/8 |

FOREIGN PATENT DOCUMENTS

WO   WO 2005/068421 A1   7/2005

OTHER PUBLICATIONS

Katz et al. ARVO Annual Meeting Abstract, 2013.*
Ang et al. "Long term effect of latanoprost on intraocular pressure in normal tension glaucoma", British Journal of Ophthalmology, vol. 88, No. 5, May 1, 2004 (May 1, 2004), pp. 630-634, XP055439995, GB ISSN: 0007-1161, DOI: 10.1136/bjo.2003.020826.
Garcia et al. "Critical evalution of latanoprostene bunod in the treatment of glaucoma", Clinical Ophthalmology, vol. 10, Oct. 1, 2016 (Oct. 1, 2016), pp. 2035-2050, XP055440083, DOI: 10.2147/OPTH.S103985.
International Search Report and Written Opinion dated Jan. 26, 2018 issued in International Application No. PCT/EP2017/078486.
Medeiros et al. "Comparison of Latanoprostene Bunod 0.024% and Timolol Maleate 0.5% in Open-Angle Glaucoma or Ocular Hypertension: The LUNAR Study", American Journal of Ophthalmology, Elsevier, Amsterdam, NL, vol. 168, May 20, 2016 (May 20, 2016), pp. 250-259, XP029663879 ISSN: 0002-09394 DOI: 10 1016/J AJO 2016 05 012.

* cited by examiner

*Primary Examiner* — Rei Tsang Shiao
(74) *Attorney, Agent, or Firm* — Arent Fox LLP

(57) ABSTRACT

This invention provides a method of lowering intraocular pressure in a patient having normal tension glaucoma, comprising contacting an eye of a subject having normal tension glaucoma with a pharmaceutical composition comprising an effective amount of Nitric Oxide releasing prostaglandin derivatives of formula (I).

7 Claims, 2 Drawing Sheets

Figure 1:
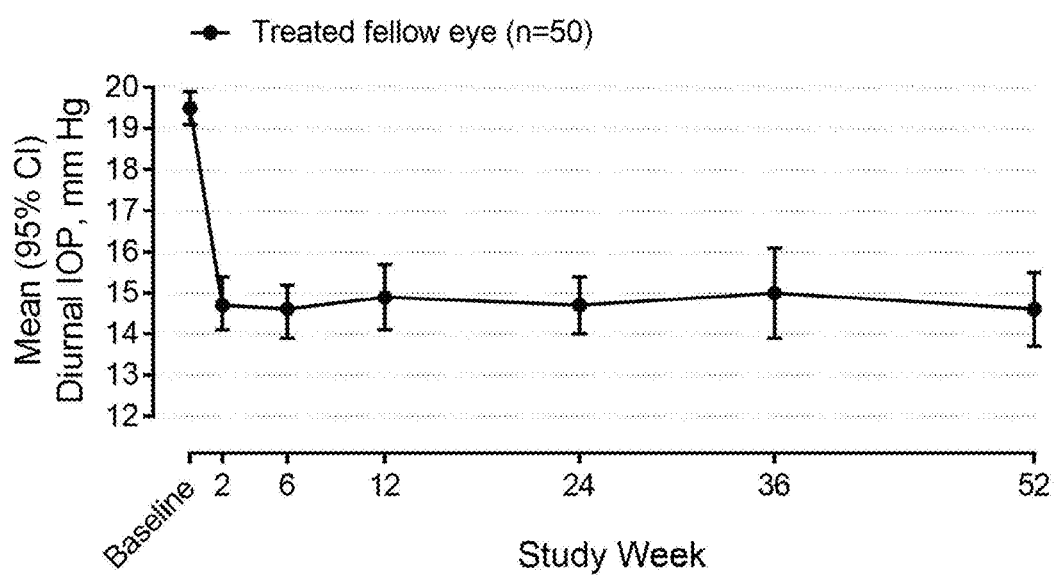

NITRIC OXIDE RELEASING PROSTAGLANDIN DERIVATIVES FOR TREATING NORMAL TENSION GLAUCOMA

CROSS-REFERENCE TO RELATED APPLICATIONS

This application is a 35 U.S.C. § 371 National Phase Entry of PCT Application No. PCT/EP2017/078486 filed Nov. 7, 2017, which claims priority to U.S. Provisional Patent Application No. 62/419,153 filed Nov. 8, 2016. The disclosures of these applications are incorporated in their entireties herein by reference.

BACKGROUND OF THE INVENTION

Normal tension glaucoma (NTG) is also referred to as low-tension glaucoma, normal-pressure glaucoma or normotensive glaucoma. NTG is a progressive optic neuropathy that mimics open-angle glaucoma, but lacks the finding of elevated intraocular pressure (IOP). NTG is a form of glaucoma in which damage occurs to the optic nerve without eye pressure exceeding the normal range. In general, a "normal" IOP range is between 12-22 mm Hg.

The causes of NTG are still unknown. Researchers continue to examine why some optic nerves are damaged by relatively low eye pressure levels. Since the causes of NTG are not known, and why normal eye pressure damages some eyes, most doctors treat normal tension glaucoma by reducing the eye pressure as low as possible using medications, laser treatments and surgical techniques.

Nitric Oxide donating prostaglandin derivatives have been studied as IOP-lowering compounds for the treatment of open-angle glaucoma (OAG) or ocular hypertension (OHT).

PCT publications WO 2005/068421, WO 2009/136281, WO 2007/000641 and WO 2007/00642 describe Nitric Oxide donating derivatives of prostaglandin $F_{2\alpha}$ analogs such as, for example, Latanoprost, Travoprost, Bimatoprost and Tafluprost. These Nitric Oxide donating prostaglandin derivatives showed a greater ocular hypotensive efficacy than their correspondent parent compounds.

Compound (1) of the present invention disclosed below, which is known as Latanoprostene Bunod (LBN), is now in clinical development for the treatment of patients with primary open-angle glaucoma (OAG) or ocular hypertension (OHT). Am J Ophthalmology 2016; Vol. 168:250-259, and Ophthalmology 2016; Vol 123(5): 965-973 disclose the results of two studies comparing the intraocular lowering effect of Latanoprostene Bunod 0.024% with timolol maleate 0.5% in subjects with open-angle glaucoma (OAG) or ocular hypertension (OHT).

Adv Ther (2016) 33: 1612-1627 discloses the results of a study that evaluated the long-term safety and intraocular pressure efficacy of Latanoprostene Bunod over one year in Japanese subjects with open-angle glaucoma or ocular hypertension.

Open-angle glaucoma is the most common form of glaucoma that is associated with an increase in the fluid pressure inside the eye and elevated intraocular pressure.

Topical prostaglandins such as latanoprost, bimatoprost, and travoprost are the first-line therapy for treating NTG. (*Br J Ophthalmol.* 2004, 88, 630-634; *Clinical Ophthalmology* 2012, 6, 1547-1552)

Alpha2 adrenergic agonists (e.g. brimonidine) carbonic anhydrase inhibitors (e.g. dorzolamide) and beta-adrenergic antagonists (e.g. timolol) are other topical agents that can be used to reduce the IOP in patients with NTG.

When monotherapy does not sufficiently reduce intraocular pressure a second-line treatment is selected to add to the prostaglandin. Even if the combination therapy may provide better pressure control than monotherapy without increasing the number of instillation, a potential concern is that the patient is exposed to the side effects of two types of drugs.

For example in elderly patients the use of beta blockers in a combination therapy should be prescribed with caution due to the potential systemic adverse effects associated with beta blockers. Certain beta blockers cause nocturnal systemic hypotension and optic nerve hypotension. (*Journal of Ophthalmology*, Vol. 2014, ID 720385, 6 pages.)

Hence, there is a need for other therapeutic agents that reduce intraocular pressure and offer efficacious and safer therapies.

The nitric-oxide releasing prostaglandin F2α analogues of the present invention showed a sustained hypotensive effect in eyes with intraocular pressure in the normal range, moreover they are dual-acting IOP lowering agent that act by increasing outflow of aqueous humor through both the trabecular meshwork and uveoscleral routes. Because of their complementary modes of action the nitric-oxide releasing prostaglandin F2α analogues of the present invention provide a better control of the pressure.

SUMMARY OF THE INVENTION

In one aspect, this invention provides a method of lowering intraocular pressure in a patient with normal tension glaucoma, comprising contacting an eye of a subject with normal tension glaucoma with a pharmaceutical composition comprising an effective amount of a Nitric Oxide releasing prostaglandin derivative of formula (I), as further described below, or a pharmaceutically acceptable salt or stereoisomer thereof.

In another aspect, this invention provides a method of treating normal tension glaucoma, comprising contacting an eye of a subject having normal tension glaucoma with a pharmaceutical composition comprising an effective amount of a Nitric Oxide releasing prostaglandin derivative of formula (I), or a pharmaceutically acceptable salt or stereoisomer thereof.

For the methods of this invention, the pharmaceutical composition may be administered as a solution, suspension or emulsion in an ophthalmic acceptable vehicle.

The pharmaceutical composition may further comprise at least one member selected from the group consisting of a beta-blocker, a carbonic anhydrase inhibitor and an adrenergic agonist.

For the methods of this invention, the intraocular pressure of the subject, prior to contacting with the pharmaceutical composition, is 12 to 22 mmHg, or no greater than 21 mm Hg, or no greater than 19 mmHg. Intraocular pressure of the subject may be lowered by at least 3 mg Hg, or at least 4 mm Hg. In addition, the lowered intraocular pressure of said subject may be sustained for at least six months, or at least one year.

For the methods of this invention, the pharmaceutical composition may be administered to said subject for at least 4 weeks, or at least 3 months, or at least 6 months, or at least 9 months, or at least 12 months.

For the methods of this invention, the pharmaceutical composition may be administered to the subject once daily, or twice daily.

In another aspect, this invention provides a method of lowering intraocular pressure in a patient having normal tension glaucoma, comprising contacting an eye of a subject having normal tension glaucoma with a pharmaceutical composition comprising an effective amount of the nitric oxide-donating prostaglandin F2α analogue (Compound (1)) having the following molecular structure, Compound (1)

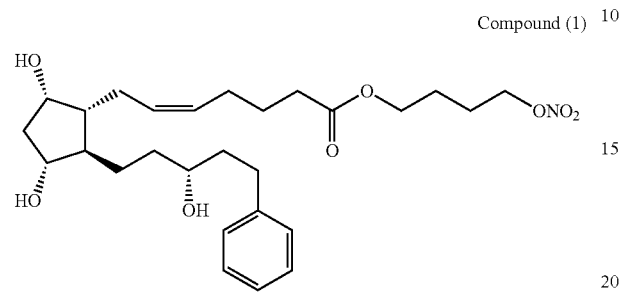

and further described below, or a pharmaceutically acceptable salt or stereoisomer thereof.

In another aspect, this invention provides a method of treating normal tension glaucoma, comprising contacting an eye of a subject having normal tension glaucoma with a pharmaceutical composition comprising an effective amount of the nitric oxide-donating prostaglandin F2α analogue (Compound (1)), or a pharmaceutically acceptable salt or stereoisomer thereof.

For the methods of this invention, the pharmaceutical composition comprising Compound (1) may be administered as a solution, suspension or emulsion in an ophthalmic acceptable vehicle.

The pharmaceutical composition may further comprise at least one member selected from the group consisting of a beta-blocker, a carbonic anhydrase inhibitor and an adrenergic agonist.

For the methods of this invention, the intraocular pressure of the subject, prior to contacting with the pharmaceutical composition, is 12 to 22 mm Hg, or no greater than 21 mm Hg, or no greater than 19 mm Hg. Intraocular pressure of the subject may be lowered by at least 3 mg Hg, or at least 4 mm Hg. In addition, the lowered intraocular pressure of said subject may be sustained for at least six months, or at least one year.

For the methods of this invention, the pharmaceutical composition comprising the nitric oxide-donating prostaglandin F2α analogue (Compound (1)) may be administered to said subject for at least 4 weeks, or at least 3 months, or at least 6 months, or at least 9 months, or at least 12 months.

For the methods of this invention, the pharmaceutical composition comprising of the nitric oxide-donating prostaglandin F2α analogue (Compound (1)) may be administered to the subject once daily, or twice daily.

DETAILED DESCRIPTION OF THE INVENTION

An object of the present invention is the use of the compound of formula (I) for lowering intraocular pressure in a patient with normal tension glaucoma, or in a method for treating normal tension glaucoma, wherein in the compound of formula (I)

$$R—X—Y—ONO_2 \quad (I)$$

R is the prostaglandin residue of formula (II):

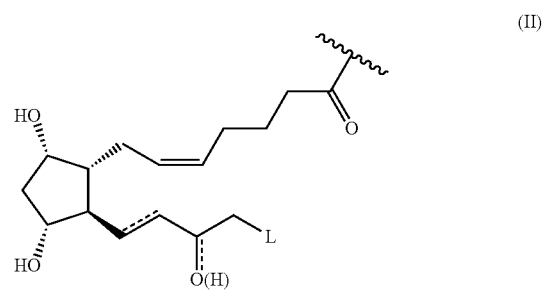

wherein the symbol $=$ represents a single bond;

L is:

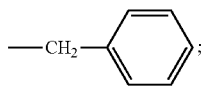

X is —O—,

Y is a bivalent radical having the following meaning: straight or branched $C_1$-$C_{10}$ alkylene, preferably $C_2$-$C_6$ alkylene.

Another object of the present invention is the use of the compound of formula (I) for lowering intraocular pressure in a patient with normal tension glaucoma, or for treating normal tension glaucoma, wherein in the compound of formula (I) R is the prostaglandin residue of latanoprost.

Another object of the present invention is the use of the compound of formula (I) for lowering intraocular pressure in a patient with normal tension glaucoma, or for treating normal tension glaucoma, wherein in the compound of formula (I) is selected from the group consisting of:

(1)

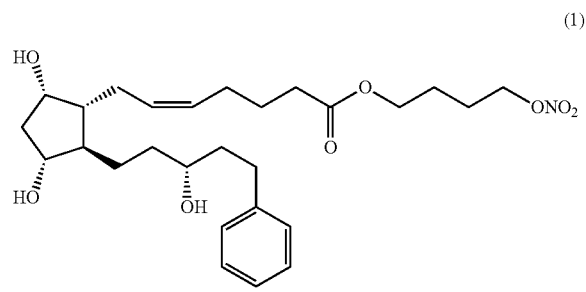

(2)

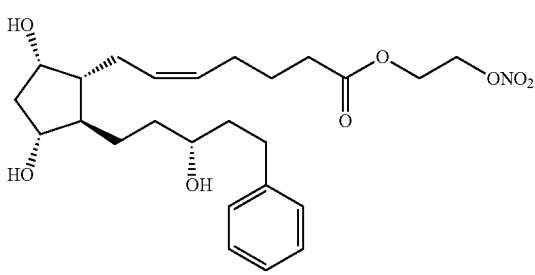

-continued (3)
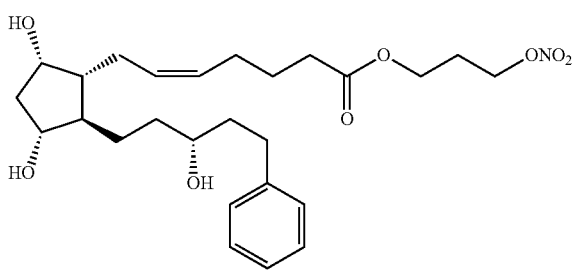

(4)
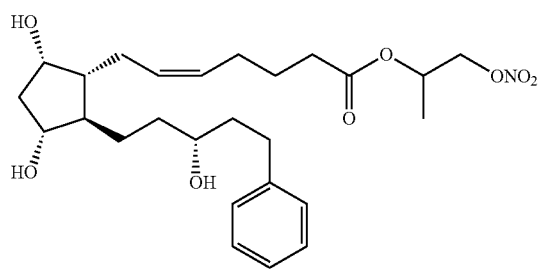

(5)
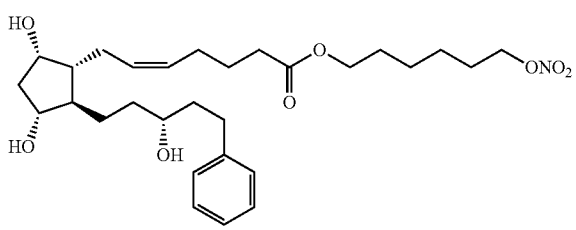

(6)
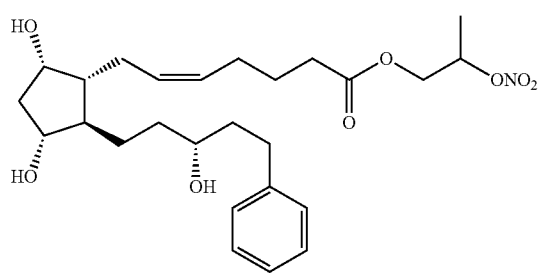

Another object of the present invention is the use of the compound of formula (I) for lowering intraocular pressure in a patient with normal tension glaucoma, or for treating normal tension glaucoma, wherein in the compound of formula (I) R is the Compound (1)

Compound (1)
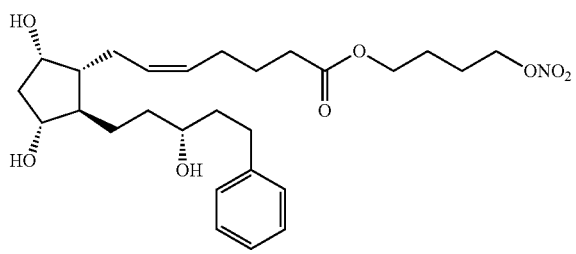

Another object of the present invention is the use of the compound of formula (I) as above defined and at least a further active principle selected from the group consisting of a beta-blocker, a carbonic anhydrase inhibitor and an adrenergic agonist for lowering intraocular pressure in a patient having normal tension glaucoma or for treating normal tension glaucoma.

Another object of the present invention is the use of Compound (1) as above defined and at least a further active principle selected from the group consisting of a beta-blocker, a carbonic anhydrase inhibitor and an adrenergic agonist for lowering intraocular pressure in a patient having normal tension glaucoma or for treating normal tension glaucoma.

The compound of formula (I) and in particular the Compound (1) can be used for lowering intraocular pressure in a patient having normal tension glaucoma or for treating normal tension glaucoma when the intraocular pressure of the patient is 12 to 22 mm Hg, or no greater than 21 mm Hg, or no greater than 19 mm Hg.

The pharmaceutical compositions comprising the compound of formula (I) as above defined are administered once daily, or twice daily for at least 4 weeks, or at least 3 months, or at least 6 months, or at least 9 months, or at least 12 months.

As mentioned above, objects of the present invention are also pharmaceutical compositions containing at least a compound of the present invention of formula (I) together with non toxic adjuvants and/or carriers usually employed in the pharmaceutical field.

The preferred route of administration is topical.

The compounds of the present invention can be administered as solutions, suspensions or emulsions (dispersions) in an ophthalmically acceptable vehicle. The term "ophthalmically acceptable vehicle" as used herein refers to any substance or combination of substances which are non-reactive with the compounds and suitable for administration to patient.

Preferred are aqueous vehicles suitable for topical application to the patient's eyes.

Other ingredients which may be desirable to use in the ophthalmic compositions of the present invention include antimicrobials, preservatives, co-solvents, surfactants and viscosity building agents.

The doses of prostaglandin nitroderivatives can be determined by standard clinical techniques and are in the same range or less than those described for the corresponding underivatized, commercially available prostaglandin compounds as reported in the: Physician's Desk Reference, Medical Economics Company, Inc., Oradell, N.J., 58$^{th}$ Ed., 2004; The pharmacological basis of therapeutics, Goodman and Gilman, J. G. Hardman, L. e. Limbird, Tenth Ed.

The compositions contain 0.1-0.30 µg, especially 1-10 µg, per application of the active compound.

The treatment may be advantageously carried out in that one drop of the composition, corresponding to about 30 µl, is administered about 1 to 2 times per day to the patient's eye.

It is further contemplated that the compounds of the present invention can be used with other medicaments known to be useful in the treatment of glaucoma or ocular hypertension, either separately or in combination. For example the compounds of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811,443. Also contemplated is the combination with nitrooxy derivatives of the above reported compounds, for example nitrooxy derivatives of beta-blockers such as those described in U.S. Pat. No. 6,242,432.

As used herein, NTG denotes a patient having an IOP range between 12 to 22 mm Hg.

NTG may be diagnosed by observing the optic nerve for signs of damage. As a first example, an ophthalmoscope is held close to the eye. In a darkened room, the light from the ophthalmoscope allows the doctor to look through the pupil and examine the shape and color of the optic nerve. A nerve that is cupped or is not a healthy pink color is a cause for concern. A second example is the visual field test. This test produces a map of the patient's complete field of vision. Using this test, the doctor can check for any areas of sight loss that may be caused by damage to the optic nerve. This would appear as slight changes in the person's vision occurring anywhere from near the center to the edge of the field of vision. These changes are not necessarily noticeable to the patient.

The compounds of the present invention can be synthesized as follows.

Synthesis Procedure

The compounds of general formula (I) as above defined, can be prepared:
i) by reacting a compound of formula (III)

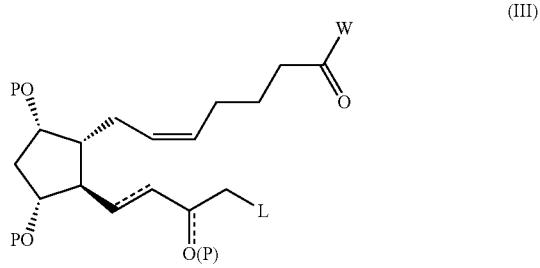

(III)

wherein
the symbol $=$ represents a single bond;
L is:

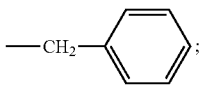

P is H or a hydroxylic protecting group such as silyl ethers, such as trimethylsilyl, tert-butyl-dimethylsilyl or acetyl and those described in T. W. Greene "Protective groups in organic synthesis", Harvard University Press, 1980, $2^{nd}$ edition, p. 14-118; W is —OH, Cl, or —OC(O)R$_1$ wherein R$_1$ is a linear or branched C$_1$-C$_5$ alkyl;
with a compound of formula (IV) Z—Y—Q wherein Y is as above defined, Z is HX or Z$_1$, being X as above defined and Zi selected from the group consisting of:
chlorine, bromine, iodine, mesyl, tosyl;
Q is —ONO$_2$ or Z$_1$ and
ii) when Q is Z$_1$, by converting the compound obtained in the step i) into nitro derivative by reaction with a nitrate source such as silver nitrate, lithium nitrate, sodium nitrate, potassium nitrate, magnesium nitrate, calcium nitrate, iron nitrate, zinc nitrate or tetraalkylammonium nitrate (wherein alkyl is C$_1$-C$_{10}$ alkyl) in a suitable organic solvent such as acetonitrile, tetrahydrofuran, methyl ethyl ketone, ethyl acetate, DMF, the reaction is carried out, in the dark, at a temperature from room temperature to the boiling temperature of the solvent. Preferred nitrate source is silver nitrate and iii) optionally deprotecting the compounds obtained in step i) or ii) as described in T. W. Greene "Protective groups in organic synthesis", Harvard University Press, 1980, $2^{nd}$ edition, p. 68-86. Fluoride ion is the preferred method for removing silyl ether protecting group.

The reaction of a compound of formula (III) wherein W=—OH and P=H, with a compound of formula (IV) wherein Y and Q are as above defined, Z is HX may be carried out in presence of a dehydrating agent as dicyclohexylcarbodiimide (DCC) or N'-(3-dimethylaminopropyl)-N-ethylcarbodiimide hydrochloride (EDAC) and a catalyst, such as N,N-dimethylamino pyridine (DMAP). The reaction is carried out in an inert organic solvent dry such as N,N'-dimethylformamide, tetrahydrofuran, benzene, toluene, dioxane, a polyhalogenated aliphatic hydrocarbon at a temperature from –20° C. and 40° C. The reaction is completed within a time range from 30 minutes to 36 hours.

The compounds of formula (III) wherein W=—OH and P=H are commercially available.

The compounds of formula (III) wherein W=—OH and P is a hydroxylic protecting group may be prepared from the corresponding compounds wherein P=H as well known in the art, for example as described in T. W. Greene "Protective groups in organic synthesis", Harvard University Press, 1980, $2^{nd}$ edition,p. 14-118.

The reaction of a compound of formula (III) wherein W=—OC(O)R$_1$ wherein R$_1$ is as above defined and P=H or a hydroxylic protecting group, with a compound of formula (IV) wherein Y is as above defined, Z is —OH and Q is —ONO$_2$ may be carried out in presence of a catalyst, such as N,N-dimethylamino pyridine (DMAP). The reaction is carried out in an inert organic solvent such as N,N'-dimethylformamide, tetrahydrofuran, benzene, toluene, dioxane, a polyhalogenated aliphatic hydrocarbon at a temperature from –20° C. and 40° C. The reaction is completed within a time range from 30 minutes to 36 hours.

The reaction of a compound of formula (III) wherein W=—OH, P=H, L is above defined, with a compound of formula (IV) wherein Y is as above defined, Z is Z$_1$ and Q is —ONO$_2$ may be carried out in presence of an organic base such as 1,8-diazabiciclo[5.4.0]undec-7-ene (DBU), N,N-diisopropylethylamine, diisopropylamine or inorganic base such as alkaline-earth metal carbonate or hydroxide, potassium carbonate, cesium carbonate, in an inert organic solvent such as N,N'-dimethylformamide, tetrahydrofuran, acetone, methyl ethyl ketone, acetonitrile, a polyhalogenated aliphatic hydrocarbon at a temperature from –20° C. and 40° C., preferably from 5° C. to 25° C. The reaction is completed within a time range from 1 to 8 hours. When Z$_1$ is chosen among chlorine or bromine the reaction is carried out in presence an iodine compound such as KI.

The reaction of a compound of formula (III) wherein W=Cl and P is as above defined, with a compound of formula (IV) wherein Y is as above defined, Z is —OH and Q is —ONO$_2$ may be carried out in presence of an organic base such as N,N-dimethylamino pyridine (DMAP), triethylamine, pyridine. The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (III) wherein W=Cl may be obtained from the corresponding acids wherein W=—OH by reaction with a thionyl or oxalyl chloride, halides of $P^{III}$ or $P^V$ in solvents inert such as toluene, chloroform, DMF.

The compounds of formula HO—Y—ONO$_2$, wherein Y is as above defined can be obtained as follows. The corresponding diol derivative, commercially available, or synthesized by well-known reactions, is converted in HO—Y—$Z_1$, wherein $Z_1$ is as above defined, by well-known reactions, for example by reaction with thionyl or oxalyl chloride, halides of $P^{III}$ or $P^V$, mesyl chloride, tosyl chloride in solvents inert such as toluene, chloroform, DMF, etc. The conversion to the nitro derivative is carried out as above described. Alternatively the diol derivative can be nitrated by reaction with nitric acid and acetic anhydride in a temperature range from −50° C. to 0° C. according to methods well known in the literature.

The compounds of formula $Z_1$—Y—ONO$_2$, wherein Y and $Z_1$ are as above defined can be obtained from the halogen derivative $Z_1$—Y—Hal, commercially available or synthesized according to methods well known in the literature, by conversion to the nitro derivative as above described.

The compounds of formula H—X—Y—$Z_1$, wherein X, Y and $Z_1$ are as above defined can be obtained from the hydroxyl derivative H—X—Y—OH, commercially available or synthesized according to methods well known in the literature, by well-known reactions, for example by reaction with thionyl or oxalyl chloride, halides of $P^{III}$ or $P^V$, mesyl chloride, tosyl chloride in solvents inert such as toluene, chloroform, DMF, etc.

Reference Example 1

Synthesis of [1R-[1α(Z), 2α(R*), 3α, 5α]]-7-[3,5-dihydroxy-2-(3-hydroxy-5-phenylpentyl)cyclopentyl]-5-heptenoic acid 4-(nitrooxy)butyl ester (compound 1)

I Synthetic Pathway

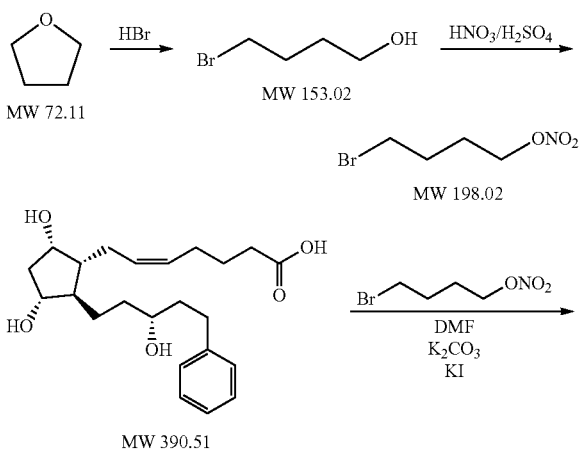

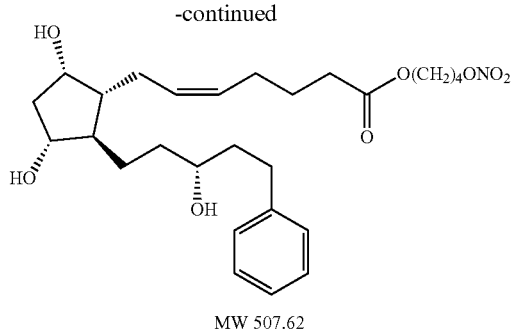

MW 507.62

II EXPERIMENTAL

II. 1 Preparation of 4-bromobutanol

Tetrahydrofuran (12.5 g-173 mmol) was charged under nitrogen in a reactor cooled to 5-10° C. Hydrogen bromide (7.0 g-86.5 mmol) was then added slowly and the reaction medium was stirred over a period of 4.5 hours at 5-10° C. The mixture was diluted with 22.5 g of cold water and the pH of this solution was adjusted to pH=5-7 by adding 27.65% sodium hydroxide (2.0 g) keeping the temperature at 5-10° C. The solution was then extracted twice with dichloromethane (13.25 g). The combined organic phases were washed with 25% brine (7.5 g), adjusted to pH=6-7 with 27.65% sodium hydroxide and dried over magnesium sulfate. Dichloromethane was distilled off and crude 4-bromobutanol (10.3 g-66.9 mmol) was obtained in a yield of about 77%.

11.2 Preparation of 4-bromobutyl nitrate

In reactor cooled to −5 to 5° C., nitric acid fuming (8.5 g-135 mmol) was slowly added to a solution of 98% sulfuric acid (13.0 g-130 mmol) in dichloromethane (18.0 g-212 mmol). 4-bromobutanol (10.2 g-66.6 mmol) was then added to this mixture and the reaction medium was stirred at −5 to 5° C. over a period of 2-5 hours. The mixture was poured into cold water (110 g) keeping the temperature between −5° C. and 3° C. After decantation, the upper aqueous phase was extracted with dichloromethane and the combined organic phases were washed with water, adjusted to pH=6-7 by addition of 27.65% sodium hydroxide, washed with brine and dried over magnesium sulfate. Dichloromethane was distilled off under vacuum and crude 4-bromobutyl nitrate (12.7 g-64.1 mmol) was recovered in a yield of about 96%.

II.3 Preparation of [1R-[1α(Z), 2β(R*), 3α, 5α]]-7-[3,5-dihydroxy-2-(3-hydroxy-5-phenylpentyl)cyclopentyl]-5-heptenoic acid 4-(nitrooxy)butyl ester Latanoprost acid (97.7%, S-isomer<1%) (213 mg, 0.54 mmol) was dissolved in 5.0 g anhydrous DMF. K$_2$CO$_3$ (206 mg, 1.49 mmol), KI (77 mg, 0.46 mmol) and 4-bromobutylnitrate (805 mg, 25% w/w in methylene chloride, 1.02 mmol) were added. The reaction mixture was heated and stirred on a rotary evaporator at 45-50° C.

After 1.5 hour, TLC (Si, CH$_2$Cl$_2$—MeOH, 5%) showed no starting acid.

The reaction mixture was diluted with 100 ml ethyl acetate, washed with brine (3×50 ml), dried over MgSO$_4$ and evaporated to give yellowish oil (420 mg).

$^1$H NMR/$^{13}$C NMR showed target molecule as a major product together with some starting 4-bromobutylnitrate and DMF.

HPLC showed no starting acid. Residual solvent, 4-bromobutylnitrate and target ester were the main peaks. Butyl nitrate ester showed similar UV spectrum as latanoprost and relative retention time was as expected.

Instrument: Bruker 300 MHz

Solvent: $CDCl_3$ $^1$H-NMR ($CDCl_3$) δ: 7.29-7.19 (5H, m, Ar); 5.45 (1H, m, CH=CH); 5.38 (1H, m, CH=CH); 4.48 (2H, t, CH2-ONO2); 4.18 (1H, m, CH—OH); 4.10 (2H, t, COOCH2); 3.95 (1H, m, CH—OH); 3.68 (1H, m, CH—OH); 2.87-2.60 (2H, m); 2.35 (2H, t); 2.25 (2H,m); 2.13 (2H,m); 1.90-1.35 (16H, m).

$^{13}$C-NMR ($CDCl_3$) ppm: 173.94 (C=O); 142.14; 129.55 (C5); 129.50 (C6); 128.50; 125.93 78.80 (C11); 74.50 (C9); 72.70 (C—ONO2); 71.39 (C15); 63.57; 52.99 (C12); 51.99 (C8); 41.30 (C10); 39.16 (C16); 33.66; 32.21; 29.73; 27.04; 26.70; 25.04; 24.91; 23.72; 15.37.

Reference Example 2

Synthesis of [1R-[1α(Z), 2β(R*), 3α,5α]]-7-[3,5-dihydroxy-2-(3-hydroxy-5-phenylpentyl) cyclopentyl]-5-heptenoic acid 3-(nitrooxy)propyl ester (compound 3).

The compound is synthesized using the procedure described for Compound 1, starting from latanoprost acid and 3-bromopropanol.

Reference Example 3

Synthesis of [1R-[1α(Z), 2β(R*), 3α,5α]]-7-[13,5-dihydroxy-2-(3-hydroxy-5-phenylpentyl) cyclopentyl]-5-heptenoic acid 2-(nitrooxy)ethyl ester (compound 2).

The compound is synthesized using the procedure described for compound 1 starting from latanoprost acid and 2-bromoethanol.

Reference Example 4

Synthesis of [1R-[1α(Z), 2β(R*), 3α,5α]]-7-[3,5-dihydroxy-2-(3-hydroxy-5-phenylpentyl) cyclopentyl]-5-heptenoic acid 6-(nitrooxy)hexyl ester (compound 5).

The compound is synthesized using the procedure described for compound 1 starting from latanoprost acid and 6-bromohexanol.

Reference Example 5

Synthesis of [1R-[1α(Z), 2β(R*), 3α,5α]]-7-[3,5-dihydroxy-2-(3-hydroxy-5-phenylpentyl) cyclopentyl]-5-heptenoic acid 2-(nitrooxy)-1-methylethyl ester (compound 4).

The compound is synthesized using the procedure described for compound 1 starting from latanoprost acid and 1-bromo-2-propanol.

Reference Example 6

Synthesis of [1R-[1α(Z), 2β(R*), 3α,5α]]-7-[3,5-dihydroxy-2-(3-hydroxy-5-phenylpentyl) cyclopentyl]-5-heptenoic acid 2-(nitrooxy)propyl ester (compound 6).

The compound is synthesized using the procedure described for compound 1 starting from latanoprost acid and 2-chloro-1-propanol.

Reference Example 7

Ophthalmic Composition Using [1R-[1α(Z), 2α(R*), 3α,5α]]-7-[3,5-dihydroxy-2-(3-hydroxy-5-phenylpentyl)cyclopentyl]-5-heptenoic acid 4-(nitrooxy) butyl ester (compound 1)

| Ingredient | Amount (mg/ml) |
| --- | --- |
| Compound 1 | 0.1 |
| Tween 80 | 5 |
| Benzalkonium chloride | 0.2 |
| Buffer | q.s. |
| water for injection | q.s. |

Buffer:
NaCl 4.1 mg/ml
$NaH_2PO_4$ (anh.) 4.74 mg/ml
$NaH_2PO_4$ (monohyd.) 4.6 mg/ml Example 1

Evaluation of the intraocular pressure (IOP) lowering effect of the nitric oxide-donating prostaglandin F2α analogue (Compound (1)) in eyes with IOP in the normal range.

1. Intraocular Pressure Lowering with Compound (1) in Eyes with Baseline IOP≤21 mm Hg The findings reported below derive from a post hoc analysis of the results of two multicenter, double-masked, parallel-group Phase 3 clinical studies that evaluated the intraocular pressure (IOP) lowering effect of a 0.024% solution of Compound (1) dissolved in vehicle in subjects with open-angle glaucoma or ocular hypertension.

Subjects≥18 years instilled one drop of a 0.024% solution of Compound (1) once daily in the evening and vehicle in the morning or timolol maleate 0.5% twice daily for 3 months (active controlled efficacy phase). Thereafter all subjects instilled Compound (1) for a further 9 months in the first study or 3 months in the second study (open-label safety extension phase).

Intraocular pressure (IOP) was measured at 8 AM, 12 PM, and 4 PM at all visits including baseline, week 2, week 6, month 3, month 6 (both studies) and months 9 and 12 (first study only).

Non-study (i.e. fellow) eyes with normal IOP at baseline treated with Compound (1) 0.024% once a day in the evening (n=50; treatment for up to 12 months) or with timolol maleate 0.5% twice a day (n=17; treatment for 3 months) were identified, and IOP outcomes were summarized using descriptive statistics and two-sided, 95% confidence intervals (CI) for the means.

Normal IOP was defined as ≤21 mm Hg (mean diurnal; average of 8 AM, 12 PM and 4 PM measurements) in the primarily Caucasian population.

Results

Compound (1) lowered IOP by 4.2-4.9 mm Hg in eyes with IOP in the normal range at baseline over the 12 months study period.

During the 3 month efficacy phase of the studies, Compound (1) lowered IOP by 4.6-4.9 mm Hg while timolol maleate lowered IOP by 3.6-4.5 mm Hg eyes with IOP in the normal range at baseline.

The results show that Compound (1) is effective for IOP lowering in eyes with IOP in the normal range and appears to be more effective than timolol maleate.

Timolol maleate is a beta-blocker and is one of the main IOP lowering agents used in the therapy for glaucoma.

FIG. 1 depicts the mean diurnal IOP in fellow eyes with baseline≤21 mm Hg (average of 8 AM, 12 PM, and 4 PM measurements) for each visit for the subjects treated with Compound (1), 0.024%.

For months 9-12 data refer to one study (n=27).

Normal IOP was defined as ≤21 mm Hg (mean diurnal) in the primarily Caucasian population.

Compound (1) lowered intraocular pressure by 4.2-4.9 mm Hg in the population having eyes with normal intraocular pressure (IOP).

The results show that Compound (1) 0.024% QD in the evening is effective for IOP lowering in eyes with IOP in the normal range.

FIG. 1 depicts the average IOP at 8 AM, 12 PM and 4 PM for each visit.

2. Intraocular Pressure Lowering with Compound (1) in Eyes with Baseline IOP≤19 mm Hg The findings reported below derive from a post hoc analysis of the results of a single-arm, multicenter, open-label Phase 3 clinical study that evaluated the IOP lowering effect of a 0.024% solution of Compound (1) dissolved in vehicle in Japanese subjects with open-angle glaucoma (including normal-tension glaucoma, pigmentary glaucoma, or pseudoexfoliative glaucoma) or ocular hypertension.

Methods

Subjects≥20 years instilled one drop of a 0.024% solution of Compound (1) once daily in the evening for 12 months. Intraocular pressure was measured at 10 AM at baseline, and every 4 weeks thereafter for a total of 13 visits. Study and non-study (i.e. fellow) eyes with normal IOP at baseline treated with Compound (1) 0.024% once a day in the evening (n=66 and n=79 for treated study and treated fellow eyes respectively) were identified, and IOP outcomes were summarized using descriptive statistics and two-sided, 95% confidence intervals (CI) for the means.

Normal IOP was defined as ≤19 mm Hg (mean IOP measured at 10 AM) in the Japanese population, since Asian populations typically have lower IOP than non-Asian populations.

Results

Compound (1) lowered IOP by 3.4-4.2 mm Hg in the study eye and 3.2-3.9 mm Hg in the treated fellow eye in the Japanese population with IOP in the normal range at baseline over the 12 months study period.

Figure 2:
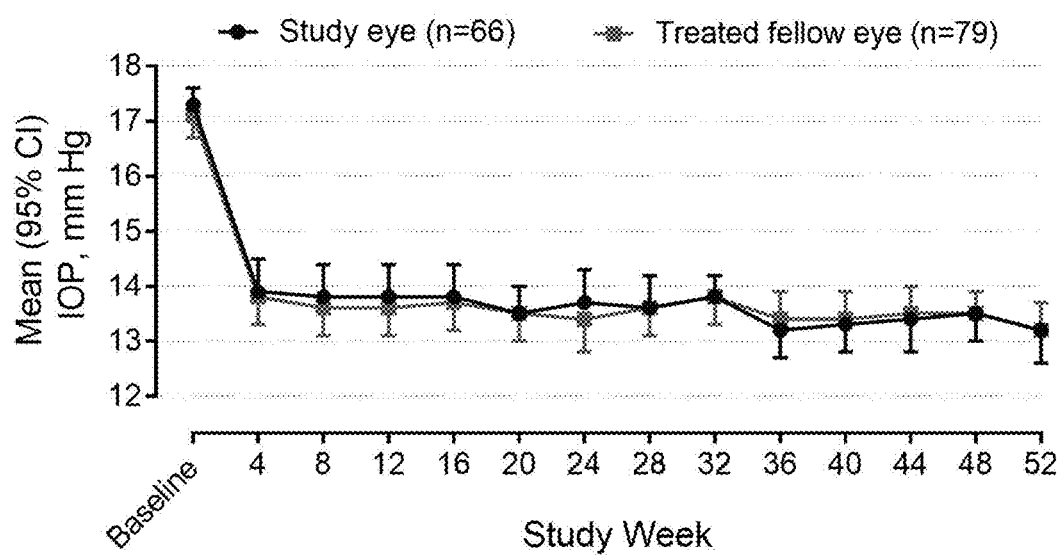

FIG. 2 depicts the mean IOP (measured at 10 AM) in treated study and non-study (fellow) eyes with baseline IOP≤19 mm Hg for each visit for the subjects treated with Compound (1), 0.024%.

The invention claimed is:

1. A method of lowering intraocular pressure in a patient with normal tension glaucoma, comprising administering to the patient a compound of formula (I), or a pharmaceutically acceptable salt or stereoisomer thereof

R—X—Y—ONO$_2$ (I)

wherein R is the prostaglandin residue of formula (II):

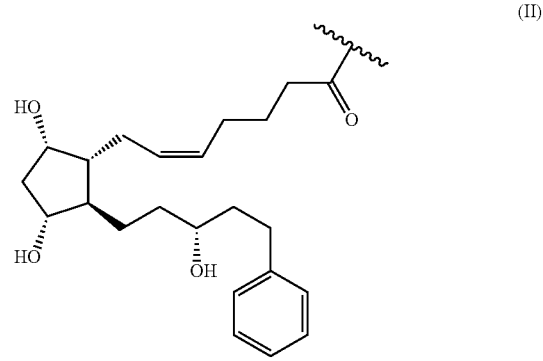

wherein

X is —O—;

Y is a bivalent radical having the following meaning:
straight or branched $C_1$-$C_{10}$ alkylene.

2. The method of claim 1, wherein the compound of formula (I) is selected from the group consisting of:

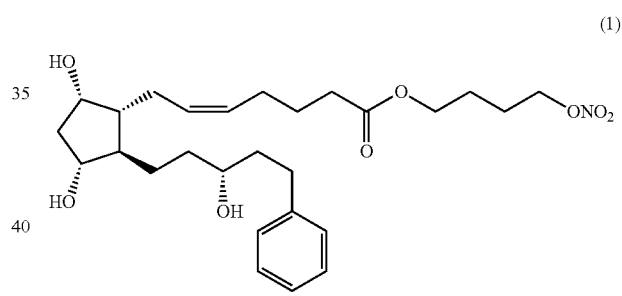

(1)

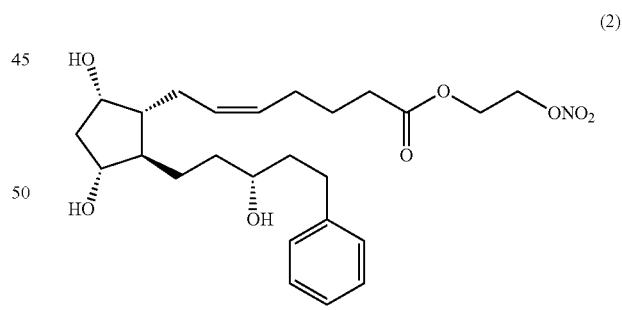

(2)

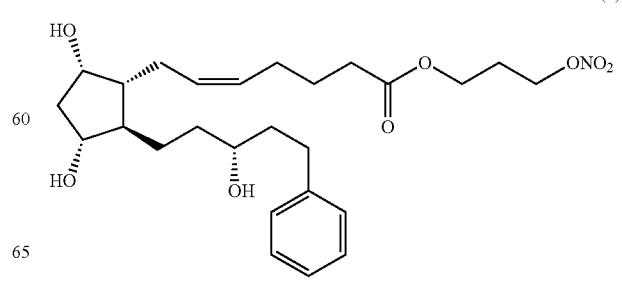

(3)

-continued

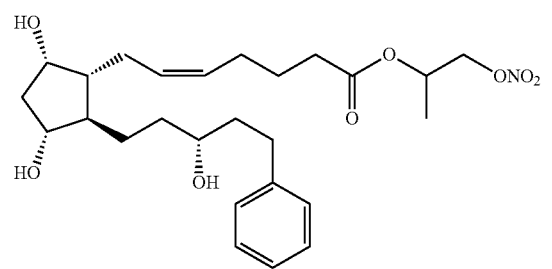
(4)

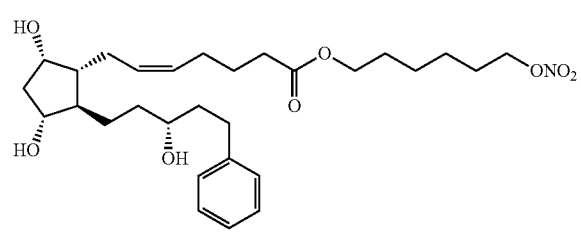
(5)

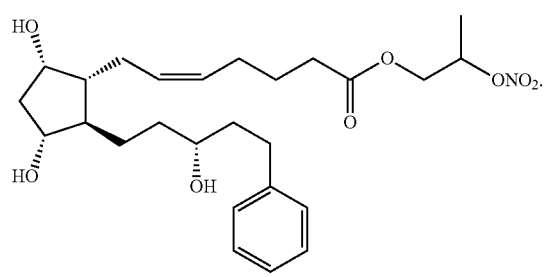
(6)

3. The method of claim 1, wherein the compound of formula (I) is compound (1).

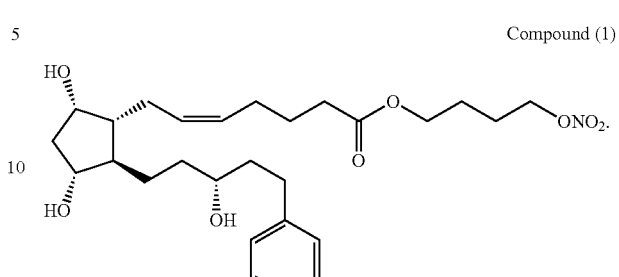
Compound (1)

4. The method of claim 1, wherein the compound of formula (I) is administered as ophthalmic pharmaceutical formulation comprising ophthalmically acceptable excipients.

5. The method of claim 1, wherein the compound of formula (I) is administered with a further active principle selected from the group consisting of a beta-blocker, a carbonic anhydrase inhibitor and an adrenergic agonist.

6. The method of claim 3, wherein compound (1) is administered with a further active principle selected from the group consisting of a beta-blocker, a carbonic anhydrase inhibitor and an adrenergic agonist.

7. The method of claim 5, wherein the compound of formula (I) and the further active principle are administered as ophthalmic pharmaceutical formulation comprising ophthalmically acceptable excipients.

\* \* \* \* \*